Dec. 26, 1972 W. H. JESSEL, JR., ET AL Plant Pat. 3,279
CHRYSANTHEMUM PLANT
Filed Feb. 3, 1971 2 Sheets-Sheet 1
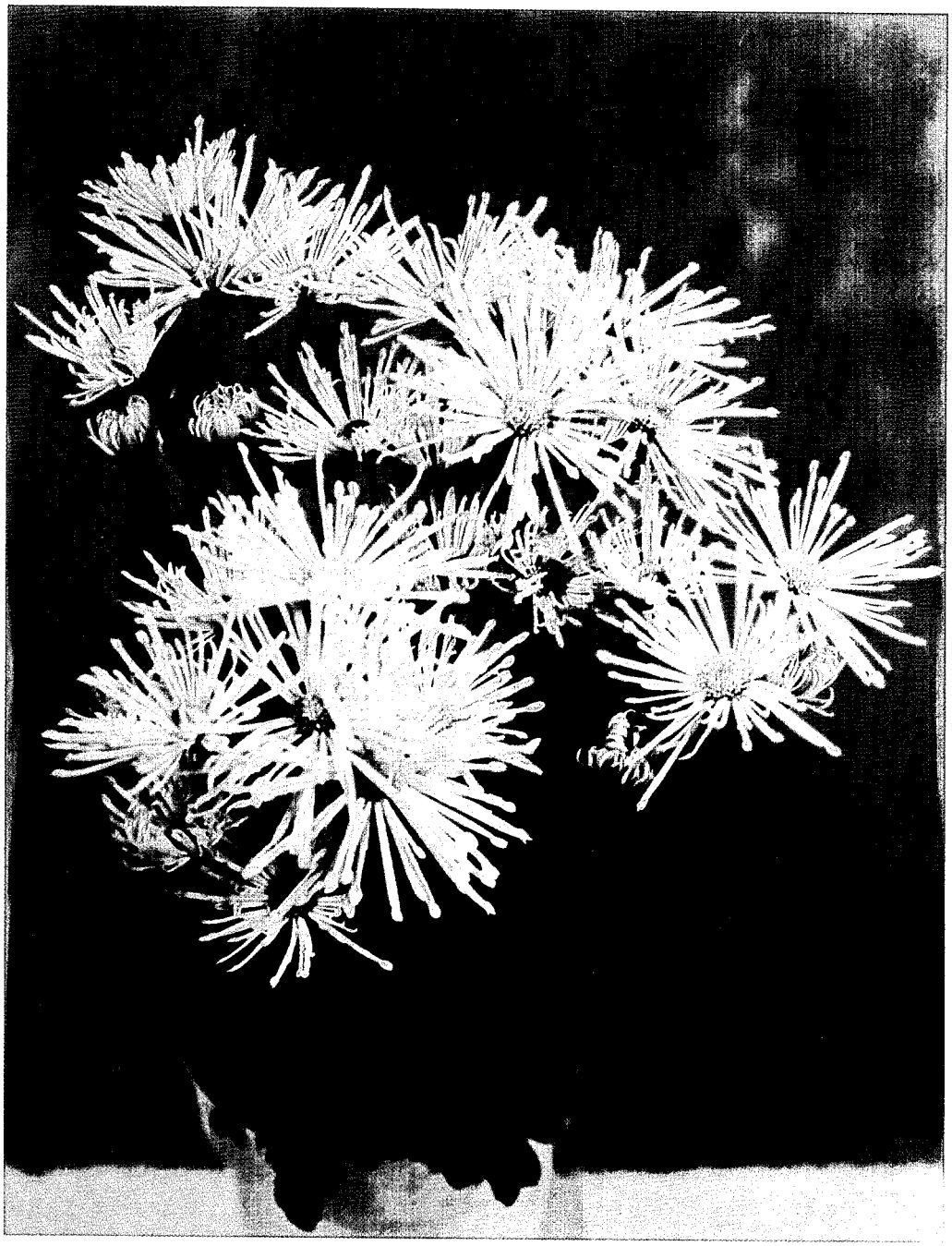
INVENTORS
WALTER H. JESSEL, JR.,
WILLIAM E. DUFFETT
BY
Oberlin, Maky, Donnelly & Renner
ATTORNEYS CHRYSANTHEMUM PLANT
Filed Feb. 3, 1971 2 Sheets-Sheet 2
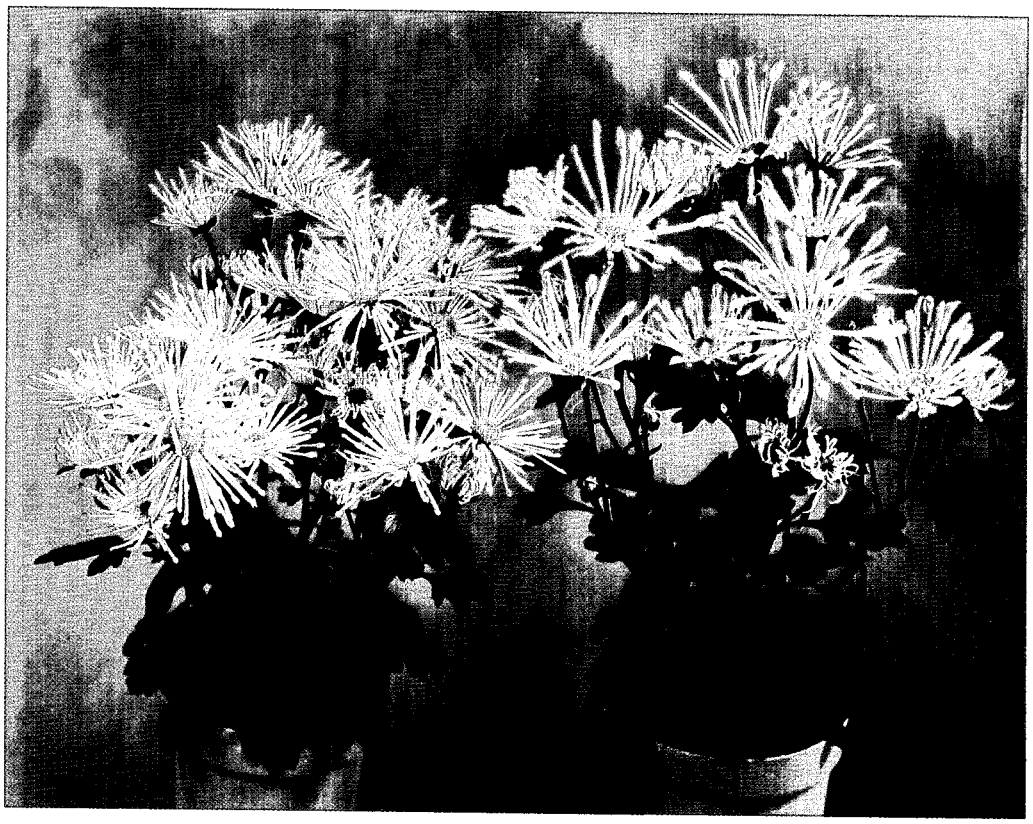
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,279

Patented Dec. 26, 1972

3,279
CHRYSANTHEMUM PLANT

Walter H. Jessel, Jr., Doylestown, and William E. Duffett, Akron, Ohio, assignors to Yoder Brothers, Inc., Barberton, Ohio

Filed Feb. 3, 1971, Ser. No. 112,489

Int. Cl. A01h *5/00*

U.S. Cl. Plt.—78 1 Claim

The present invention comprises a new and distinct cultivar of chrysanthemum plant which is a seedling of #365×#2720. Both of these parents are unpatented and are identified for breeding purposes by the above numbers to distinguish the same from other parents in the same breeding program.

The new cultivar is adaptable to natural outdoor flowering in the fall or to spring pot flowering in the greenhouse. The new cultivar is similar in certain respects to Shining Light, an unpatented but commercial cultivar of Yoder Brothers, Inc., Barberton, Ohio, having the same characteristics as Shining Light of a seven week response as an outdoor variety, and its generally yellow color.

The new cultivar is distinguished from Shining Light by the following characteristics:

(1) ½" smaller flowers.

(2) Darker, more opaque golden yellow flower color.

(3) Fewer disc or perfect florets.

(4) Less pollen.

(5) 3–4" shorter habit; more dense and prolific.

(6) Less indented foliage with less serration to the leaf edge.

(7) Brighter green foliage.

(8) Due to shorter, more dense habit, the new cultivar resists lodging or falling over outdoors better than Shining Light.

(9) Better frost tolerance.

(10) Twice the number of breaks from a pinch, therefore producing a fuller, denser plant even though total spread or diameter is approximately the same.

(11) In natural flowering outdoors, it flowers 2–3 days earlier.

(12) In spring pots, flowering in the greenhouse in May, it is more uniform in response and produces a more compact and shapely pot.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the entire United States is from March through May, and September and October.

The accompanying drawings show the unique characteristics of the new cultivar, the color being as nearly true as possible with color illustrations of this type. Sheet 1 shows the new cultivar by itself and sheet 2 comprises a comparison view of the new cultivar and the comparison cultivar Shining Light, with the latter appearing on the right and the new cultivar on the left.

In the description which follows, color references are to the Munsell Color Book, 1963 edition, and comparisons have been made with the cultivar Shining Light. Where only the value or description of the new cultivar appears, such value or description applies also to the comparison cultivar.

BOTANICAL CLASSIFICATION: *Chryanthemum morifolium*

| | Sunburst Cushion | Shining Light |
|---|---|---|
| Bloom: | | |
| Size | 1¾" | 2¼". |
| Fully expanded | 2⅜" | 2⅝". |
| Borne | Clusters on elongated pedicels | |
| Stems | Strong | |
| Form | Quilled spoon | |
| Permanence | 14–20 days | |
| Color: | | |
| Center of flower | Yellow, 5Y8/14 | Yellow, 2.5Y8.5/10. |
| Base of petals | Dark yellow, 2.5Y8/12 | Yellow, 2.5Y8/12. |
| Inside of petals | Dark yellow, 2.5Y8/14 | Do. |
| Reverse of petals | do | Do |
| Tonality from a distance | Golden yellow | Dark yellow. |
| Discoloration | do | Do. |
| Petals: | | |
| Texture | Smooth | |
| Appearance and form | Tubular—flatten at apex to a pointed spoon | |
| Arrangement | Composite, whorled on a single Receptacle | |
| Persistence | Resist shatter | |
| Fragrance | Typical chrysanthemum | |
| Reproductive organs: | | |
| Stamen, anthers | 10–40 | 30–60. |
| Pollen | Scant to moderate | Moderate to abundant. |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | Herbaceous. |
| Growth | Spreading | Spreading—semiupright. |
| Height | Approximately 15" when flowered naturally as field grown plants from a planting made in mid-June and given a single pinch in late June. | Approximately 18" when flowered naturally as field grown plants from a planting made in mid-June and given a single pinch in late June. |
| Spread | Approximately 25" when flowered naturally as field grown plants from a planting made in mid-June and given a single pinch in late June. | Approximately 24" when flowered naturally as field grown plants from a planting made in mid-June and given a single pinch in late June. |
| Foliage: | | |
| Top side | Dark green, 7.5GY4/6 | Dark green, 7.5GY4/4. |
| Size | 3⅞" long, 2⅛" wide | 2½" long, 1⅝" wide. |
| Quantity | Numerous | Numerous. |
| Shape | Spatulate lobed | Spatulate lobed. |
| Texture | Smooth | Smooth. |
| Ribs and veins | Prominent | Prominent. |
| Edge | Moderately indented | Indented. |
| Serration | Very slight | Moderate. |
| Under side | Light green, 7.5GY5/4 | Light green, 7.5GY5/4. |
| Stipules | Rudimentary | Rudimentary. |

We claim:

1. A new and distinct cultivar of chrysanthemum characterized particularly as to its uniqueness when compared to the cultivar Shining Light by its ½″ smaller flowers, darker, more opaque golden yellow flower coloration, fewer disc or perfect florets, less pollen, 3–4″ shorter, and its more dense and prolific habit, thereby providing more resistance to lodging or falling over outdoors, less indented foliage with less serration, brighter green foliage, better frost tolerance, approximately twice the number of breaks from a pinch therefore producing a fuller, denser plant even though the spread or diameter is approximately the same, its 2–3 days earlier natural flowering outdoors, and its more compact and shapely pot habit when used in a spring pot flowering program in the greenhouse.

No references cited.

ROBERT BAGWILL, Primary Examiner